United States Patent [19]

Wiedemann et al.

[11] Patent Number: 5,448,792
[45] Date of Patent: Sep. 12, 1995

[54] TOOTHBRUSH

[75] Inventors: Wolfgang U. Wiedemann, Höchberg, Germany; Piet C. J. Van Rens, Eindhoven, Netherlands; Norbert Schneider, Ebental, Austria

[73] Assignee: U.S. Philips Corporation, New York, N.Y.

[21] Appl. No.: 249,406

[22] Filed: May 26, 1994

[30] Foreign Application Priority Data

May 28, 1993 [EP] European Pat. Off. ............ 93201536

[51] Int. Cl.⁶ .................. A61C 17/34; A46B 13/02
[52] U.S. Cl. ............................. 15/22.1; 74/23
[58] Field of Search .......... 15/22.1, 22.2, 22.4; 74/23, 111; 310/50

[56] References Cited

U.S. PATENT DOCUMENTS

| | | | |
|---|---|---|---|
| 3,379,906 | 4/1968 | Spohr | 15/22.1 |
| 3,588,936 | 6/1971 | Duve | 15/22.1 |
| 4,710,995 | 12/1987 | Joyashiki et al. | 15/22.1 |

FOREIGN PATENT DOCUMENTS

| | | | |
|---|---|---|---|
| 0004358 | 1/1977 | Japan | 15/22.1 |
| 5023217 | 2/1993 | Japan | 15/22.1 |

*Primary Examiner*—Edward L. Roberts, Jr.
*Attorney, Agent, or Firm*—Ernestine C. Bartlett

[57] ABSTRACT

A tooth-brush is provided which has a brush shank (4) adapted to be driven electrically by a drive (2) and provided with a brush-head (5) having bristles (6), which brush-head performs movement (8), for example, a loosening movement whose frequency is higher than 30 Hz and whose amplitude is between 0.1 mm and 5 mm, which brush-head performs an additional movement (9), for example, a wiping movement having a frequency of between 1 Hz and 5 Hz. The combination of a rapid loosening movement and a slow wiping movement ensures that the teeth are cleaned in a thorough but gentle manner.

12 Claims, 3 Drawing Sheets

TOOTHBRUSH

FIELD OF THE INVENTION

The invention relates to a tooth-brush having a brush shank adapted to be driven electrically by a drive means and provided with a brush-head having bristles, which brush-head performs a movement, for example, a loosening movement, whose frequency is higher than 30 Hz.

BACKGROUND OF THE INVENTION

For cleaning the teeth, in order to loosen dental film or plaque on the tooth surfaces, numerous electrically driven toothbrushes are available, performing different brushing movements. These vary from a planar elliptical movement of the bristle ends with a major axis of approximately 2 mm and a minor axis of approximately 10 mm, via an oscillatory movement of the brush surface about the longitudinal axis of the handle, and a combination of an oscillatory movement and a short axial movement of 1-2 mm, to a rotation of cylindrical tufts of bristles about their longitudinal axes. A further group of electrically driven mechanical tooth-cleaning appliances effects cleaning by a rotation of the individual tufts of bristles and/or a combination of this movement with a pivotal movement of the entire brush. The movement frequency is generally between 20 and 50 Hz.

As a result of the rapid reciprocatory movement of the brush the cleaning action is effective only at those spots which as a rule are readily accessible at any rate, i.e. the surfaces of the teeth.

The combination of large amplitudes with brush movement frequencies of between 20 and 50 Hz leads to the following symptoms or drawbacks:

- At step-like surface structures, for example at the transition between the gingival border and the tooth, blind corners are formed where the bristle ends do not reach the surface to be cleaned. As a result, these areas are not cleaned or not cleaned properly.
- Owing to the large amplitude associated with the high frequency the brush behaves as a brush whose individual filaments are less flexible and dynamically stiffer. The maximum force exerted on, for example, the gums then exceeds the now generally accepted permissible value of approximately 2 N and leads to gum injury.
- Some of the bristles get caught and are almost immobilized, exerting an impermissible pressure on the gums when the brush passes through the center position.
- The interdental spaces are not cleaned satisfactorily because the bristles do not reach into the interdental spaces as a result of their dynamic stiffening. The bristles remain on the prominent tooth surfaces so that the deeper situated interdental spaces and the approximal surfaces are skipped. Neither do they reach into the gingival sulcus.

The cleaning action of the tooth-brush decreases distinctly at lower frequencies. Moreover, as the frequency decreases the feel of the tooth-brush diminishes, which also leads to poor cleaning results.

With tooth-brushes of the above-mentioned type having separately rotating tufts the interdental spaces are cleaned but an undesired side-effect of these brushes is that they cause a substantial attrition of the dentine at the tooth necks.

SUMMARY OF THE INVENTION

It is an object of the invention to construct a toothbrush in such a way that even hard-to-reach areas of the tooth surfaces can be cleaned in a very thorough but gentle manner.

This object is achieved in that a toothbrush is provided which has a brush head which performs two movements, a first movement the amplitude of which is between 0.1 mm and 5 mm, and wherein the brush-head performs an additional, second movement having a frequency of between 1 Hz and 5 Hz. For simplicity of discussion, as used herein said first movement is referred to as the loosening movement, and said second movement is referred to as the wiping movement.

Films on the tooth surfaces are loosened by the rapid and small movements of the brush-head. As a result of the rapid and small loosening movements the individual bristles can also penetrate the hard-to-reach areas of the teeth and detach the plaque by an oscillating movement. Owing to the small amplitude the dynamic stiffening of the bristles is only minimal, so that gum injury is avoided. The slow additional movement wipes the loosened film off the tooth. This slow wiping movement also prevents the individual bristles from being caught in the dental recesses. Moreover, the slow wiping movement causes the position of the bristles relative to the teeth to change, resulting in a very effective cleaning. The slow wiping movement of the brush-head is imparted to the bristle ends, which results in the bristle ends having an amplitude of between 2 and 10 mm.

Owing to the rapid small movements the bristle ends on the tooth surfaces and the gums are never at rest but have a substantial velocity so that the reactive force for the slow movement is constituted merely by the force of the friction with which the bristles slide on the dental enamel and the gums. These small reactive forces are still easy to compensate by hand even at low frequencies.

It has proved to be advantageous if the loosening movement is a rectilinear reciprocating movement in the direction of the longitudinal axis of the brush shank with a frequency of between 60 Hz and 70 Hz and an amplitude of approximately 2 mm, and in that the wiping movement is an oscillatory movement about the longitudinal axis of the brush shank with a frequency of between 2 Hz and 3 Hz and with an overall angular excursion of 10° to 30°.

Generally, the bristle ends will readily follow the brush-head movement. For the wiping movement of the bristle ends this means an amplitude of between 2 and 2.5 mm. Experience has shown that these frequencies and amplitudes are found to be pleasant during cleaning and that the cleaning result is satisfactory.

A preferred embodiment of the invention is characterized in that the brush shank is adapted to be coupled to a tooth-brush shaft which is drivable by an electric motor, which tooth-brush shaft is drivable in the direction of the oscillatory movement and in the direction of the reciprocating movement by means of an eccentric mechanism, which eccentric mechanism comprises two eccentric pins which are each guided in a recess in the tooth-brush shaft to drive the tooth-brush shaft in the direction of the oscillatory movement and in the direction of the reciprocating movement, respectively, and each have a speed corresponding to said frequency.

Preferably, a reduction mechanism is provided between the two eccentric pins.

It has proved to be advantageous if the reduction mechanism is formed by a two-stage eccentric planetary gear mechanism.

In another preferred construction the reduction mechanism is formed by a worm gear mechanism.

The invention will now be described in more detail with reference to the drawings, which show some exemplary embodiments.

DETAILED DESCRIPTION OF THE PREFERRED EMBODIMENTS

Figure 1:
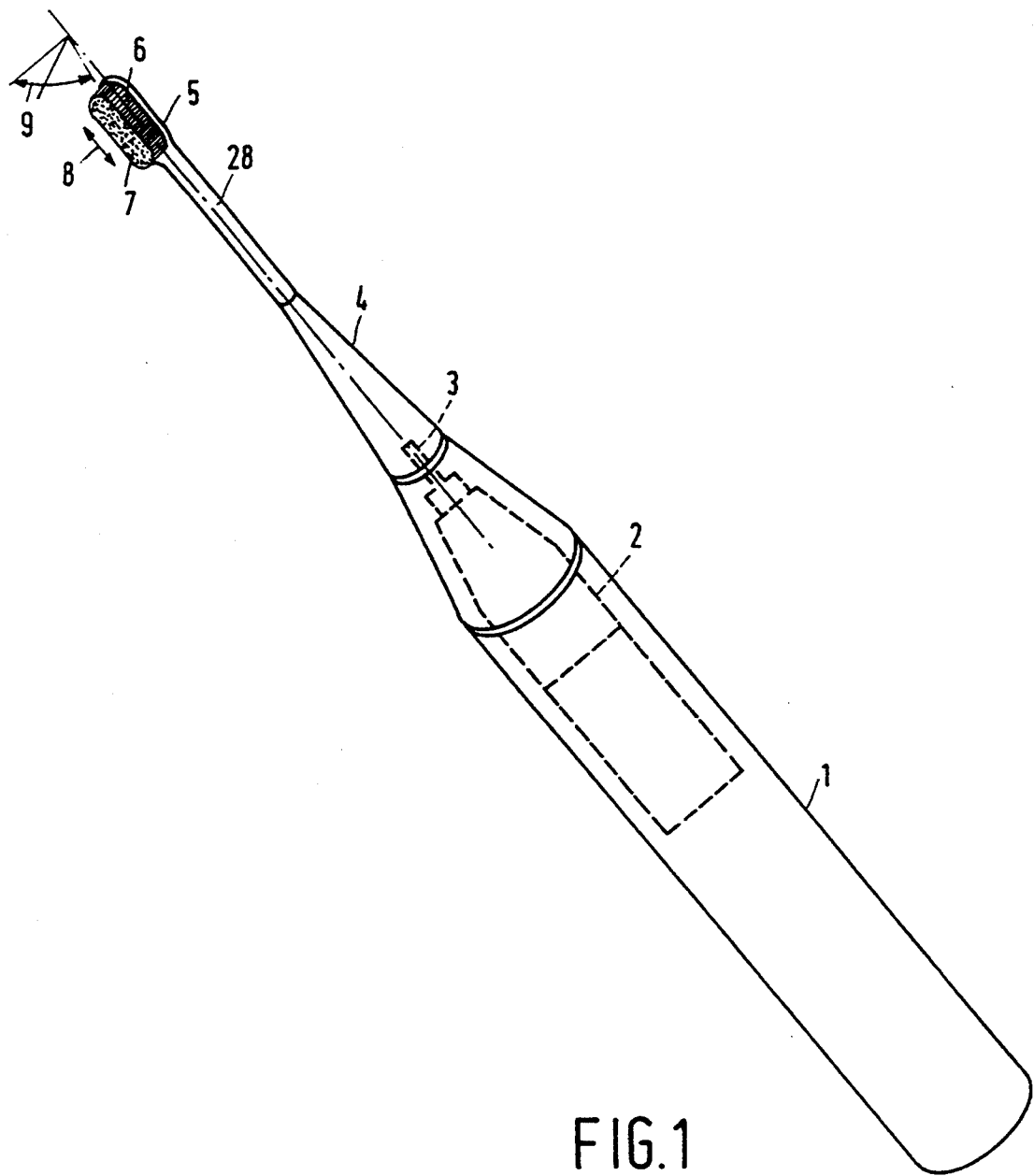
FIG. 1 is an oblique view of a tooth-brush in accordance with the invention.

The tooth-brush shown in FIG. 1 basically comprises a rod-shaped housing 1, which accommodates a drive means 2 and which also functions as a handle. The drive means has a tooth-brush shaft 3, which projects from the housing. A brush shank 4 carrying a brush-head 5 is detachably coupled to the tooth-brush shaft 3, for example, by means of a snap connection. The brush-head carries a multitude of bristles 6. In accordance with the invention the brush-head performs a first movement 8 having a frequency higher than 30 Hz and having an amplitude of between 0.1 and 5 mm, this movement being superimposed on a second movement 9 having a substantially lower frequency, i.e. between 1 and 5 Hz.

Figure 2:
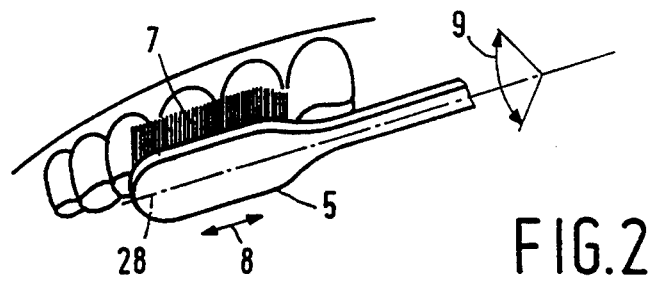
FIG. 2 shows the movements of the brush relative to the teeth.

FIG. 2 shows the position of the brush relative to the teeth. The overall movement of the brush-head is imparted to the bristle ends 7. The rapid first movement loosens dental plaque and, for simplicity, it is referred to hereinafter as the loosening movement 8. The slow second movement wipes the loosened plaque off the teeth and, for simplicity, it is referred to hereinafter as the wiping movement 9.

Figure 3:
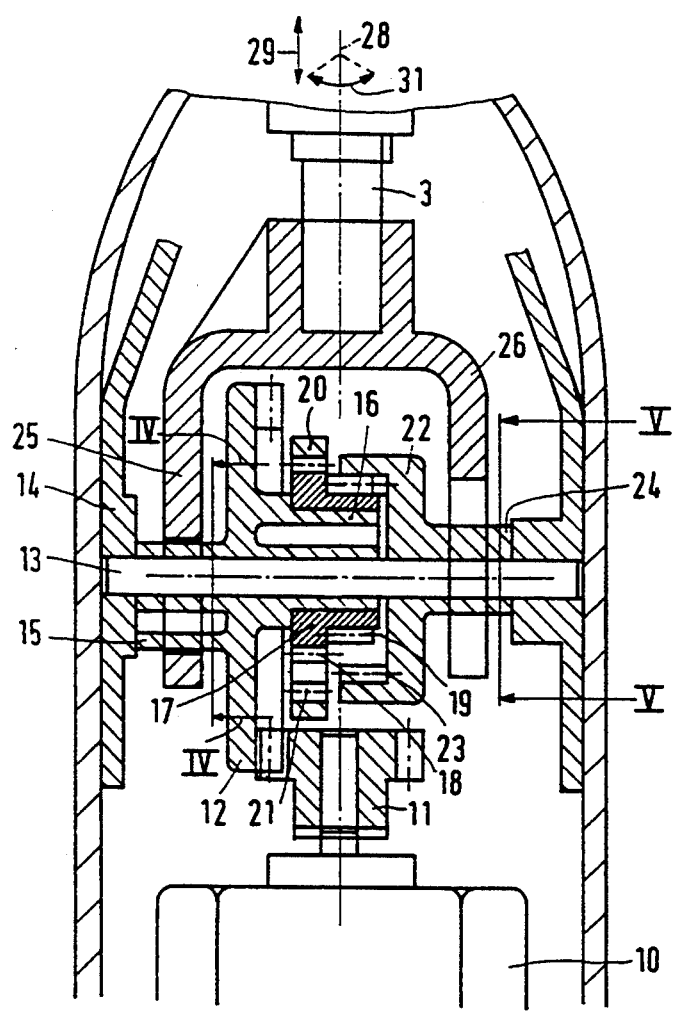
FIG. 3 diagrammatically shows the drive means of a first embodiment to an enlarged scale.

FIG. 3 shows the drive means for realizing these two movements with their respective frequencies. A motor 10 drives a crown wheel 12 via a pinion 11. This crown wheel is journalled on a shaft 13. The shaft 13 is mounted in a frame 14. The crown wheel carries two eccentrics 15 and 16. The eccentric 16 carries a double toothed wheel 17. This double toothed wheel has two toothed rims 18 and 19 having different numbers of teeth. A ring 20 having inner teeth 21 is fixedly mounted in the frame 14. The toothed rim 18 of the double toothed wheel 17 is made to roll over the inner teeth 21 of the ting by means of the eccentric 16. A toothed wheel 22 having inner teeth 23 is journalled on the shaft 13, which is secured in the housing. The toothed wheel 22 further carries an eccentric 24. The toothed rim 19 of the double toothed wheel 17 is made to roll over the inner teeth 23 of the toothed wheel 22 by means of the same eccentric 16. By a suitable choice of the number of teeth it is possible to obtain the desired reduction of the speed of the crown wheel 12 relative to the toothed wheel 22, i.e. the speed of the toothed wheel 22 relative to the crown wheel 12 is reduced by a factor of 25.

Figure 4:
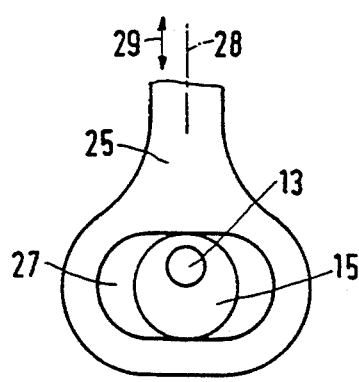
FIG. 4 is a sectional view taken on the line IV—IV in FIG. 3.
Figure 5:
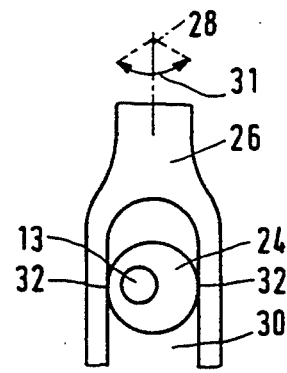
FIG. 5 is a sectional view taken on the line V—V in FIG. 3.

The output shaft 3 of the tooth-brush is journalled in the frame 14 and has two arms 25 and 26 which are radially spaced from and fixedly connected to the tooth-brush shaft. The arm 25 has an elongate opening 27 (see FIG. 4), the longitudinal axis of the opening extending transversely of the longitudinal axis 28 of the tooth-brush shaft 3 and the brush shank 4. The eccentric 15 engages the opening 27, as is also shown in FIG. 4. The eccentric movement of the eccentric 15 on the crown wheel 12 results in a linear reciprocating movement 29 of the arm 25 and, consequently, of the tooth-brush shaft 3, which movement has an amplitude (stroke) dictated by the magnitude of the eccentricity of the eccentric 15. This movement causes said loosening movement 8 of the bristle ends 7. The arm 26 has an elongate opening 30 (see FIG. 5), the longitudinal axis of the opening extending parallel to the longitudinal axis 28 of the tooth-brush shaft 3 and the brush shank 4. The eccentric 24 provided in the toothed wheel 22 engages the elongate opening 30. The elongate opening 30 has one open end to simplify mounting. As a result of the movement of the eccentric 24 the arm 26 and, consequently, the tooth-brush shaft 3 experience an oscillating movement 31 about the longitudinal axis 28. This movement causes said wiping movement 9 of the bristle ends 7. As a result, the wiping movement is a reciprocating circular-arc movement. The amplitude of this oscillatory wiping movement depends on the magnitude of the eccentricity of the eccentric 24, on the distance between the arm 26 and the longitudinal axis 28 of the brush shank 4, and on the distance between the bristle ends 7 and the longitudinal axis 28. Obviously, the edges of the elongate opening 30 should be rounded so as to permit the desired oscillating movement.

In the example shown in FIG. 3 the frequency of the loosening movement is approximately 60 Hz and the stroke is approximately 2 mm, the frequency of the wiping movement being approximately 2.4 Hz for an oscillatory angular rotation of approximately 10°, which corresponds to a stroke of approximately 2 mm of the bristle ends.

It is obvious that other transmissions are also possible, for example a transmission between the two eccentrics 15 and 24 can be realized by means of a single eccentric planetary drive. A toothed wheel having 24 teeth cooperates with a toothed wheel having 25 inner teeth by means of an eccentric, which yields a very compact drive with a ratio of 1:25.

Figure 6:
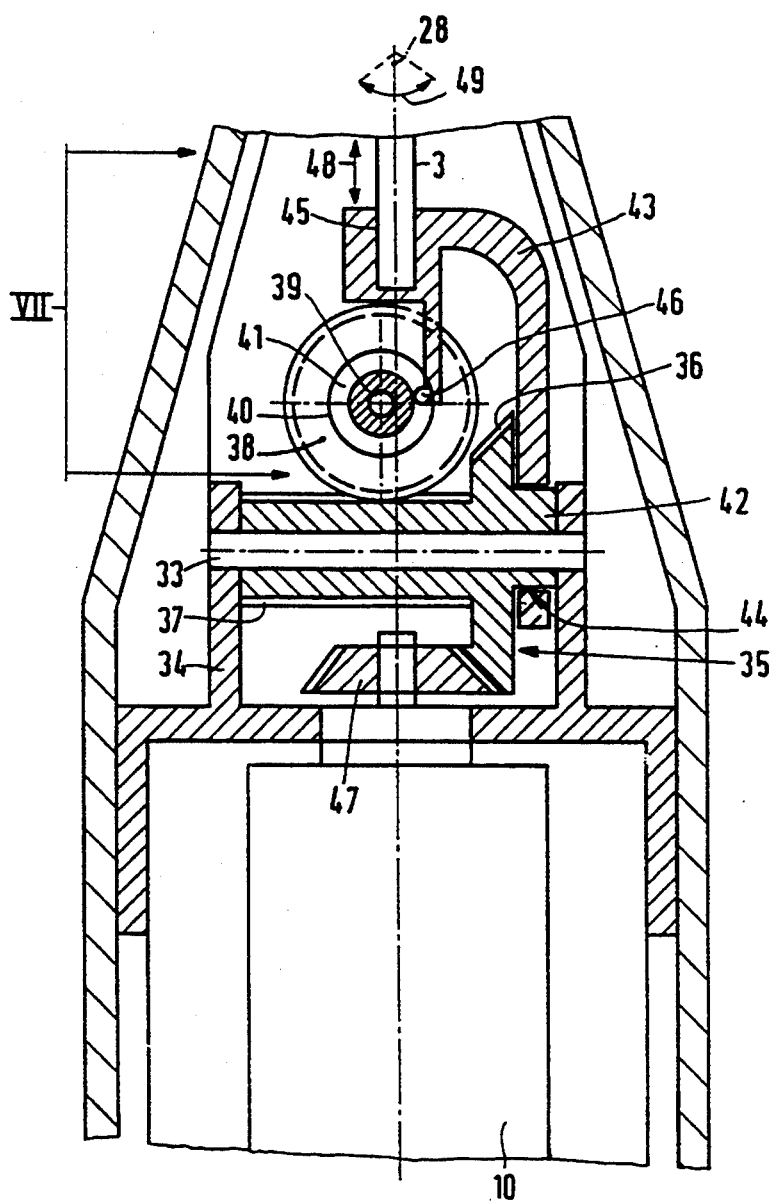
FIG. 6 diagrammatically shows the drive means of a second embodiment to an enlarged scale.
Figure 7:
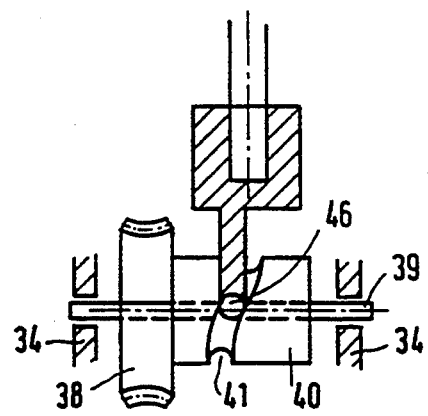
FIG. 7 is a sectional view taken on the line VII—VII in FIG. 6.

FIG. 6 shows another drive means for realizing the two movements with different frequencies. In this case a worm drive is used. A shaft 33 is mounted in a frame 34. A toothed wheel 35, which consists of a bevel wheel 36 and a worm 37, is rotatably journalled on the shaft 33. The worm 37 is in mesh with a worm wheel 38. The worm wheel 38 is rotatably supported on a shaft 39 secured in the housing. The worm wheel carries a stud 40, which rotates with the worm wheel about the shaft 39. The stud 40 has a sinusoidal groove 41. The toothed wheel 35 further has an eccentric 42. An arm 43 has a longitudinal opening 44 at one side, the longitudinal axis of the opening extending transversely of the longitudinal axis 28 of the tooth-brush shaft 3. The eccentric 42 engages this opening 44. The other side of the arm 43 has an opening 45. A lower end portion of the toothbrush shaft is fixedly mounted in this opening. The arm also comprises a cam follower 46 which engages the cam groove 41 and cooperates therewith. A motor 10 drives the toothed wheel 35 via a bevel pinion 47, which toothed wheel drives the worm wheel 38 with the stud 40 by means of the worm drive. The worm drive ensures that the rotation of the stud 40 is, for example, 25 times as slow as the toothed wheel 35 with the eccentric 42. The rotation of the eccentric produces a linear reciprocating movement 48 of the tooth-brush shaft 3 in the direction of the longitudinal axis 28. At the same time, the cooperation between the follower 46 and the rotating groove 41 generates an oscillatory movement 49 of the tooth-brush shaft 3 about its longitudinal axis 28. The reciprocating movement 48 corresponds to said loosening movement 8 and the oscillatory movement 49 corresponds to said wiping movement 9 of the bristle ends 7, which wiping movement is 25 times as slow as the loosening movement if the transmission ratio of the worm drive is 1:25.

Both the rapid loosening movement and the slow wiping movement may be composed of a plurality of motions, such as a translation and/or rotation.

Various mechanisms are available to provide the drive for the rapid loosening movement. In most cases rotary or vibrating-armature motors are used. Other drive mechanisms, such as for example the use of the piezo-effect, are conceivable. The corresponding movements can also be generated by an actuation such that the entire tooth-brush in the hand of the user is an oscillatory system which is caused to oscillate, for example, via an unbalanced rotary motor. The drive for the slow wiping movement can be provided by planar circular and elliptical movements, elliptical movements based on axial oscillatory and linear excursions, pure oscillatory movements, pure axial movements or also rotary movements. Moreover, the two movements may each be produced by means of a single motor with a suitable drive mechanism.

An essential feature is that the loosening movement and the wiping movement have a translation or rotation frequency corresponding to the specified frequency ranges, the amplitudes of the relevant combined movements being adapted to the dimensions of the teeth.

We claim:

1. A tooth-brush having a brush shank adapted to be driven electrically by a drive means and provide with a brush-head having bristles, which drive means is effective via said brush shank to drive said brush-head to perform a first movement whose frequency is higher than 30 Hz, the amplitude of the first movement being between about 0.1 mm and about 5 mm, and a second movement having a frequency of between about 1 Hz and about 5 Hz.

2. A tooth-brush as claimed in claim 1, wherein the first movement is a rectilinear reciprocating movement in the direction of the longitudinal axis of the brush shank with a frequency of between 60 Hz and 70 Hz and an amplitude of approximately 2 mm, and the second movement is an oscillatory movement about the longitudinal axis of the brush shank with a frequency of between 2 Hz and 3 Hz and with an overall angular excursion of 10° to 30°.

3. A tooth-brush as claimed in claim 2, wherein the brush shank is adapted to be coupled to a tooth-brush shaft which is drivable by an electric motor, which tooth-brush shaft is drivable in the direction of the oscillatory movement and in the direction of the reciprocating movement by means of an eccentric mechanism, which eccentric mechanism comprises two eccentric pins which are each guided in a recess in the toothbrush shaft to drive the tooth-brush shaft in the direction of the oscillatory movement and in the direction of the reciprocating movement, respectively, and each have a speed corresponding to said frequency.

4. A tooth-brush as claimed in claim 3, wherein a reduction mechanism is provided between the two eccentric pins.

5. A tooth-brush as claimed in claim 4, wherein the reduction mechanism is formed by a two-stage eccentric planetary gear mechanism.

6. A tooth-brush as claimed in claim 4, wherein the reduction mechanism is formed by a worm gear mechanism.

7. A tooth-brush having a housing which contains a drive means having a brush shaft, a brush shank having a longitudinal axis carrying a brush head detachably coupled to the brush shaft, and provided with a brush-head having bristles, the drive means being effective via said brush shank to drive said brush-head to cause first and second movements of the brush-head, the first movement having a frequency that is higher than the frequency of said second movement resulting in a relatively rapid movement for loosening material to be removed from teeth being brushed, and the second movement has a substantially lower frequency than the frequency of said first movement resulting in a relatively slow movement for wiping the material loosened from teeth brushed during said first movement.

8. A tooth-brush as claimed in claim 7, wherein the frequency of said first movement is higher than 30 Hz, the amplitude of the loosening first movement is between about 0.1 mm and about 5 mm, and the frequency of the second movement is between about 1 Hz and about 5 Hz.

9. A tooth-brush as claimed in claim 7, wherein the first loosening movement is a rectilinear reciprocating movement in the direction of the longitudinal axis of the brush shank with a frequency of between 60 Hz and 70 Hz and an amplitude of approximately 2 mm, and the second movement is an oscillatory movement about the longitudinal axis of the brush shank with a frequency of between 2 Hz and 3 Hz and with an overall excursion of 10° to 30°.

10. A tooth-brush as claimed in claim 9, wherein the brush shank is adapted to be coupled to a tooth-brush shaft which is drivable by an electric motor, which tooth-brush shaft is drivable in the direction of the oscillatory movement and in the direction of the reciprocating movement by an eccentric mechanism, which eccentric mechanism comprises two eccentric pins which are each guided in a recess in the tooth-brush shaft to drive the tooth-brush shaft in the direction of the oscillatory movement and in the direction of the reciprocating movement, respectively, each pin having a speed corresponding to said frequency.

11. A tooth-brush having a housing which contains a drive means having a brush shaft, a brush shank carrying a brush-head detachably coupled to the shaft, and provided with a brush-head having bristles, the drive means being effective via said brush shank to drive said brush-head to cause first and second movements of the brush-head, the first movement having a frequency that is higher than the frequency of said second movement resulting in a relatively rapid movement for loosening material to be removed from teeth being brushed, and the second movement has a substantially lower frequency than the frequency of said first movement resulting in a relatively slow movement for wiping the material loosened from teeth brushed during said first movement;

wherein the frequency of said first movement is higher than 30 Hz, the amplitude of the first movement is between about 0.1 mm and about 5 mm, and the frequency of the second movement is between about 1 Hz and about 5 Hz; and wherein the first loosening movement is a rectilinear reciprocating movement in the direction of the longitudinal axis of the brush shank, and the second movement is an oscillatory movement about the longitudinal axis of the brush shank with an overall excursion of 10° to 30°; and wherein the brush shank is adapted to be coupled to a tooth-brush shaft which is drivable by an electric motor, which tooth-brush shaft is drivable in the direction of the oscillatory movement and in the direction of the reciprocating movement by an eccentric mechanism, which eccentric mechanism comprises two eccentric pins which are each guided in a recess in the tooth-brush shaft to drive the tooth-brush shaft in the direction of the oscillatory movement and in the direction of the reciprocating movement, respectively, each pin having a speed corresponding to said frequency.

12. A tooth-brush as claimed in claim 11, wherein the frequency of the first movement is between 60 Hz and 70 Hz and an amplitude of about 2 mm, and the frequency of the second movement is between 2 Hz and 3 Hz.

* * * * *